United States Patent
Bashkirov et al.

(10) Patent No.: US 7,081,619 B2
(45) Date of Patent: Jul. 25, 2006

(54) NANODOSIMETER BASED ON SINGLE ION DETECTION

(75) Inventors: Vladimir Bashkirov, Loma Linda, CA (US); Reinhard W. Schulte, Grand Terrace, CA (US); Sergei Shchemelinin, Rehovot (IL); Amos Breskin, Nes Ziona (IL); Rachel Chechik, Moshav Bet Hanan (IL); Guy Garty, Rehovot (IL); Jamie Milligan, San Diego, CA (US)

(73) Assignees: Loma Linda University, Loma Linda, CA (US); Yeda, Ltd., Rehovot (IL)

( * ) Notice: Subject to any disclaimer, the term of this patent is extended or adjusted under 35 U.S.C. 154(b) by 0 days.

(21) Appl. No.: 10/894,873

(22) Filed: Jul. 20, 2004

(65) Prior Publication Data
US 2005/0109929 A1    May 26, 2005

Related U.S. Application Data

(63) Continuation of application No. 10/258,704, filed as application No. PCT/US01/13624 on Apr. 27, 2001, now Pat. No. 6,787,771.

(60) Provisional application No. 60/200,533, filed on Apr. 27, 2000.

(51) Int. Cl.
*H01J 49/40* (2006.01)
(52) U.S. Cl. .................. 250/286; 250/283; 250/287
(58) Field of Classification Search ............... 250/286, 250/283, 287, 281, 282
See application file for complete search history.

(56) References Cited

U.S. PATENT DOCUMENTS 3,621,240 A    11/1971    Cohen et al.

FOREIGN PATENT DOCUMENTS

WO    WO 87/00682    1/1987

(Continued)

OTHER PUBLICATIONS

Shehemelinin S. et al., "First Measurements of Jonisation Clusters on the DNA Scale in a Wall-Less Sensitive Volume," *Radiation Protection Dosimetry*, (1999), vol. 82, No. 1, pp. 43-50. Nuclear Technology Publishing.

(Continued)

*Primary Examiner*—Kiet T. Nguyen
(74) *Attorney, Agent, or Firm*—Knobbe, Martens, Olson & Bear, LLP.

(57) ABSTRACT

A nanodosimeter device (15) for detecting positive ions induced in a sensitive gas volume by a radiation field of primary particle, comprising an ionization chamber (10) for holding the sensitive gas volume to be irradiated by the radiation field of primary particles; an ion counter system connected to the ionization chamber (10) for detecting the positive ions which pass through the aperture opening and arrive at the ion counter (12) at an arrival time; a particle tracking system for position-sensitive detection of the primary particles passing through the sensitive gas volume; and a data acquisition system capable of coordinating the readout of all data signals and of performing data analysis correlating the arrival time of the positive ions detected by the ion counter system relative to the position sensitive data of primary particles detected by the particle tracking system. The invention further includes the use of the nanodosimeter for method of calibrating radiation exposure with damage to a nucleic acid within a sample. A volume of tissue-equivalent gas is radiated with a radiation field to induce positive ions. The resulting positive ions are measured and compared with a determination of presence or extent of damage resulting from irradiating a nucleic acid sample with an equivalent dose of radiation.

17 Claims, 15 Drawing Sheets

U.S. PATENT DOCUMENTS

| | | | |
|---|---|---|---|
| 4,517,462 | A | 5/1985 | Boyer et al. |
| 4,831,254 | A | 5/1989 | Jenkins |
| 4,931,653 | A | 6/1990 | Hamm et al. |
| 5,026,988 | A | 6/1991 | Mendenhall et al. |
| 5,061,850 | A | 10/1991 | Kelly et al. |
| 5,128,543 | A * | 7/1992 | Reed et al. .................. 250/287 |
| 5,256,879 | A | 10/1993 | McNulty et al. |
| 5,306,918 | A | 4/1994 | Goudonnet et al. |
| 5,347,132 | A | 9/1994 | Holzmann et al. |
| 5,596,199 | A | 1/1997 | McNulty et al. |
| 5,777,325 | A | 7/1998 | Weinberger et al. |
| 5,981,946 | A | 11/1999 | Mason |
| 6,242,737 | B1 | 6/2001 | Ohnishi et al. |
| 6,417,515 | B1 | 7/2002 | Barrett et al. |

OTHER PUBLICATIONS

Shchemelinin S. et al., "Ionization measurements in small gas samples by single ion counting," (1996), pp. 859-861, Nuclear Instruments and Methods in Physics Research A 368.

Ambrosio M. et al., "The Time-Track Complementarity Approach in the EAS-TOP Experiment," (1998), pp. 315-317, Nuclear Physics B, Proceedings Supplements, (Mar. 1999).

Dixit, M.S., et al., "Development of Gas Microstrip Detectors for Digital X-Ray Imaging and Radiation Dosimetry," 1998, pp. 809-813, IEEE Transactions on Instrumentation and Measurement, IEEE Inc. New York, US. vol. 47, No. 3.

Shchemelinin, A. et al., "A Nanodosimeter Based on Single Ion Counting," (1997), pp. 375-378, in Goodhead, et al., "Microdosimetry, An Interdisciplinary Approach".

"Research Team Hopes to add New Dimension to Clinical Proton Therapy and Radiobiology," excerpts from Proton Treatment Center Newsletter, vol. 8, No. 1, 1998, on web at www.llu.edu/proton/physician/news/nano/htm.

"Modeling of Radiation Action Based on a Nanodosimetric Event Specter," Schulte, et al., Poster Presentation at the Eleventh Annual Investigators' Workshop in Space Radiation Research, May 27-31, 2000, published on the web Apr. 18, 2000.

* cited by examiner

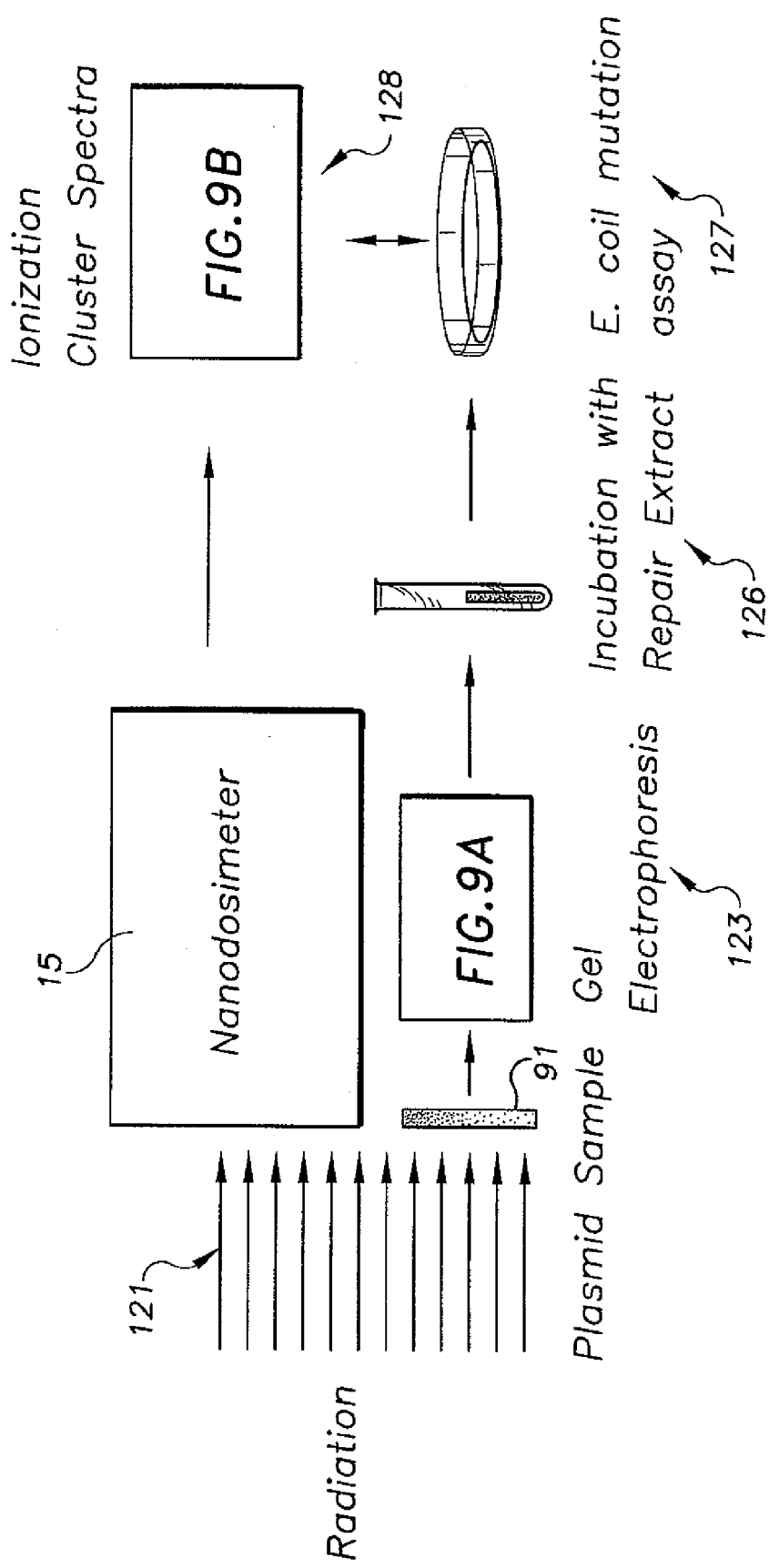

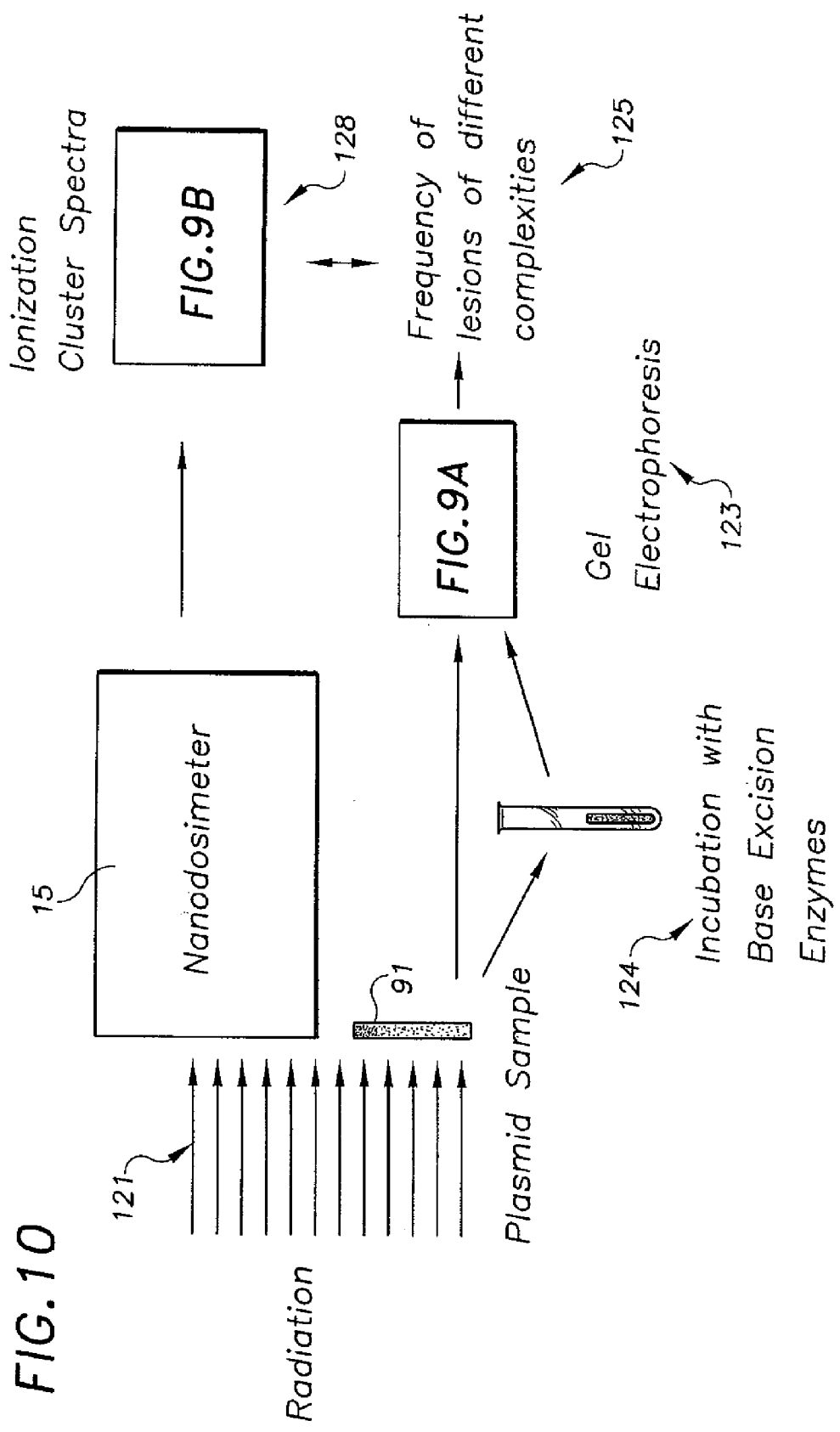

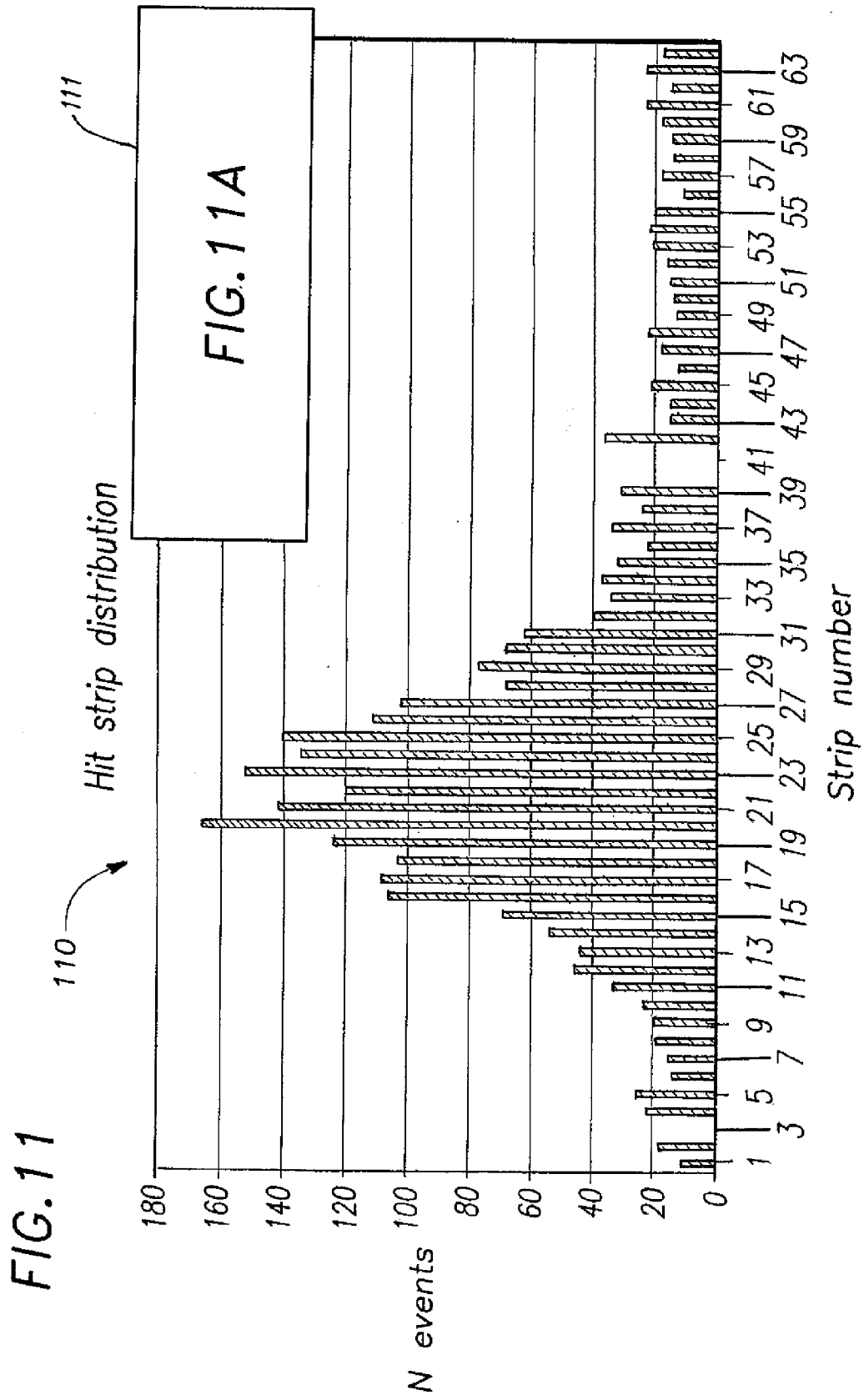

NANODOSIMETER BASED ON SINGLE ION DETECTION

CROSS-REFERENCE TO RELATED APPLICATIONS

This application is a continuation of U.S. patent application Ser. No. 10/258,704, titled "Nanodosimeter Based on Single Ion Detection," filed Oct. 25, 2002, now U.S. Pat. No. 6,787,771, which is national stage application (35 U.S.C. § 371) of PCT International Application Serial No. PCT/US01/13624, titled "Nanodosimeter Based on Single Ion Detection." filed Apr. 27, 2001, which claims priority from U.S. Provisional Patent Application Ser. No. 60/200,533, titled "Nanodosimeter Based on Single Ion Detection," filed Apr. 27, 2000. The contents of each of the aforementioned U.S. Patent Applications are hereby incorporated in their entirety into this disclosure by reference.

STATEMENT REGARDING FEDERALLY SPONSORED RESEARCH OR DEVELOPMENT

This invention was made with Government support under cooperative agreement number DAMD17-97-2-7016 with the United States Department of the Army. The Government has certain rights in this invention.

BACKGROUND OF INVENTION

According to modern radiobiological concepts, irreversible radiation damage to a living cell is the consequence of multiple ionizations occurring within or near the DNA molecule over a distance of a few nanometers. Such clustered ionization events can lead to multiple molecular damages within close proximity, some of them causing strand breakage and others various base alternations or losses, which are difficult to repair. Unrepaired or misrepaired DNA damages typically lead to cell mutations or cell death.

The measurement of the number and spacing of individual ionizations in DNA-size volumes can be assumed to one of the most relevant for the specification of what can be termed "radiation quality." By radiation quality, we refer to measurable physical parameters of ionizing radiation that best correlate to the severity of biological effects caused in living organisms. There are a variety of practical applications for such measurements in radiation protection and monitoring, as well as in radiotherapy.

The monitoring and measurement of radiation quality and the investigation of how it relates to the biological effects of ionizing radiation is of prime importance in many different fields including medicine, radiation protection, and manned space flight. For example, heavy charged particles, including protons, carbon ions, and neutrons produce more complex radiation fields than established forms of radiation therapy (protons and electrons). These newer forms of radiation therapy, which are increasingly being used for the treatment of cancer, require a careful study of radiation quality changing with penetration depth in order to avoid unwanted side effects.

The definition of the merits and risks of these new forms of radiotherapy requires a better understanding of the basic interactions these radiations have with DNA. National and international radiation and environmental protection agencies, e.g., the Nation Council on Radiation Protection and Measurements (NCRP) and the International Commission on Radiological Protection (ICRP), are interested in establishing new standards of radiation quality measurements, which are based on individual interactions of radiation with important biomolecules, most importantly, the DNA.

Further, radiation quality measurements are also essential to predict the risks of human space travel. Predictions of the quality and magnitude of space radiation exposure are still subject to large uncertainties. Nanodosimetric measurements of space radiations or simulated ground-based radiations may help to decrease these uncertainties.

The measurement of local ionization clusters in DNA-size volumes requires the development of novel nanodosimetric devices, as these would be most relevant to assess DNA damage. The results of experimental nanodosimetric studies combined with those of direct radiobiological investigations could provide a better understanding of the mechanisms of radiation damage to cells and the reason why some DNA damage is more serious than others leading to cancer or cell death. They would also provide valuable input for biophysical models of cellular radiation damage. There are a variety of practical applications for such measurements in radiation protection and monitoring, as well as in radiotherapy.

Existing methodologies of dosimetry on a microscopic tissue-equivalent scale use microdosimetric gas detectors, for example, tissue-equivalent proportional counters (TEPCs), which measure the integral deposition of charges induced in tissue-equivalent spherical gas volumes of 0.2–10 μm in diameter, i.e., at the level of metaphase chromosomes and cell nuclei. They cannot be used to measure ionizations in volumes simulating the DNA helix. Furthermore, they provide no information about the spacing of individual ionizations at the nanometer level.

The cavity walls of these microdosimetric counters distort the measurements, which is particularly problematic for cavity sizes below the track diameter. It has been suggested to use wall-less single-electron counters to overcome some of these limitations. However, this method is limited by the fairly large diffusion of electrons in the working gas and can only achieve sensitive volume sizes down to the order of ten tissue-equivalent nanometers. The DNA double helix, on the other hand, has a diameter of 2.3 nm.

It has been suggested in the literature to overcome the limitations of microdosimetric counters through the construction of a dosimeter which would combine the principle of a wall-less sensitive volume with the advantage of counting positive ionization ions, which undergo considerably less diffusion than electrons. This would extend classical microdosimetry into the nanometer domain.

This method, called nanodosimetry, is useful for radiobiology based on the premise that short segments of DNA (approximately 50 base pairs or 18 run long) and associated water molecules represent the most relevant surrogate radiobiological targets for study. Instead of measuring the deposition of charges directly in biological targets, nanodosimetry uses a millimeter-size volume filled with a low-density gas at approximately 1 Torr pressure, ideally, of the same atomic composition as the biological medium. Ions induced by ionizing radiation in the working gas are extracted by an electric field through a small aperture and then accelerate towards a single-ion counter. The sensitive volume of the detector is defined by the gas region from which positive radiation-induced ions can be collected using electric-field extraction. This new method would be useful for determining the biological effectiveness of different radiation fields in the terrestrial and extraterrestrial environment.

The problem with prior nanodosimeters, therefore, is that they have lacked means for measurement of the energy and multi-axis position-sensitive detection of primary particles passing through the nanodosimeter, hindering the ability to perform systematic measurements of ionization clusters within a cylindrical tissue-equivalent volume as a function of these important parameters. Further, a method for calibration of a nanodosimeter, e.g., correlating radiation quality with biological damage, has been unavailable. Therefore, the goals of nanodosimetery described above have been a long felt, but as yet unmet need.

It would be desirable, therefore, to have a nanodosimeter which includes a particle tracking and energy measuring system that is capable of multi-axis position-sensitive detection of primary particles passing through the detector within the nanodosimeter, thereby providing the ability to perform systematic measurements of ionization clusters within a cylindrical tissue-equivalent volume as a function of the position of the primary particle and its energy. Once configured with such a particle tracking and energy measuring system, it would be desirable to be able to calibrate the nanodosimeter to correlate the radiobiological data of DNA damage to radiation quality, thereby relating the physics of energy deposition to radiobiological effects.

SUMMARY OF INVENTION

The present invention meets these needs by providing a nanodosimeter which includes a particle tracking and energy measuring system that is capable of multi-axis position-sensitive detection of primary particles passing through the detector within the nanodosimeter, and of energy measurement of these primary particles. Using the particle tracking and energy measuring system; a method of calibrating the nanodosimeter to correlate the radiobiological data of DNA damage to radiation quality, thereby relating the physics of energy deposition to radiobiological effects, is also provided.

Use of a MWP detector, or preferably a silicon microstrip detector, is provided, as well as a data acquisition system to run such a nanodosimeter, and thereby process primary particles and secondary ionizations on an event-by-event basis. The provided system is able to measure the energy of primary particle, and detect the location of primary particles, and allow on-line reduction of very large statistical samples, capable of simultaneous detection and counting of particles The apparatus and method measure individual ions produced by ionizing particles in a wall-less, low-pressure gas volume, which simulates a biological sample of nanometer dimensions. Changing pressure conditions, the size of the sensitive volume can be modified. Modifying the electrical field configuration inside the detector, also the shape of the sensitive volume can be adjusted. The detector registers the number of ions produced in the sensitive volume as well as their spacing along the principal axis of the sensitive volume; both quantities are believed to be important for the biological effectiveness of terrestrial and extraterrestrial radiation. The new detector can be used to provide input data of biophysical models that can predict the biological efficiency or quality of the radiation under investigation. Another novel aspect of the device is that almost any gas composition can be used in order to study radiation effects in the various subcompartments of the biological system, e.g., water and DNA.

BRIEF DESCRIPTION OF DRAWINGS

These and other features, aspects, and advantages of the present invention will become better understood with reference to the following description, appended claims, and accompanying drawings, where:

FIG. 10 is a pictorial flow chart representing a calibration method according to another embodiment of the present invention;

DETAILED DESCRIPTION

The present invention will be better understood with respect to FIGS. 1–11 that accompany this application.

Figure 1B:
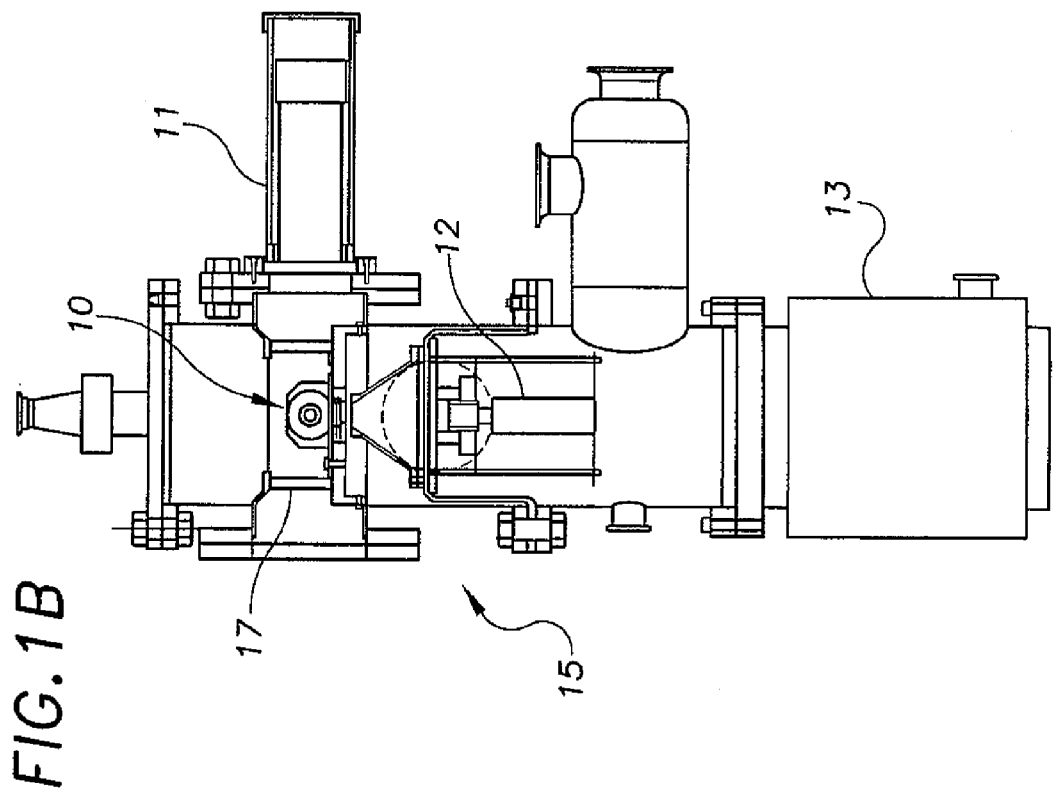
FIG. 1B is a cross-sectional diagram of a side view of the nanodosimeter of FIG. 1A.
Figure 1A:
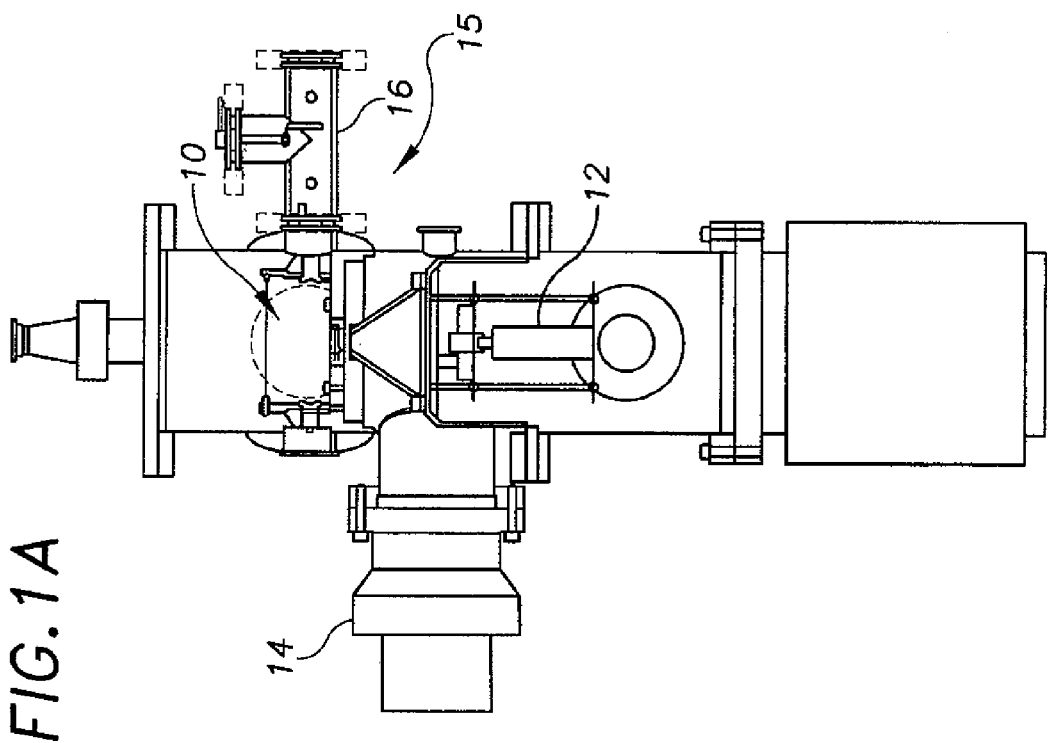
FIG. 1A is a cross-sectional diagram of a front view of a nanodosimeter capable of being used with the present invention.

FIGS. 1A and 1B show detailed drawings of a nanodosimeter 15 that is capable of being used with the present invention, comprising an ionization chamber 10 holding a low-pressure gas, into which radiation is injected either from a built-in a particle source 16 which is in communication with the ionization chamber, or from any external radiation source after passing through an entrance window 17, a detector 11 and an ion counter 12 for counting ionized particles. A differential pumping system comprising two pumps 14 and 15 is also provided to maintain a relatively low pressure (e.g., a high vacuum) in the chamber holding the ion counter, while maintaining a higher pressure within the ionization chamber. Any suitable radiation source emitting ionized charged particles with sufficient energy to penetrate window 17 can be used, as will be evident to those skilled in the art. Any suitable detector 11 can be used, such as a scintillator-photomultiplier tube (PMT) combination, as will also be evident to those skilled in the art.

Figure 2:
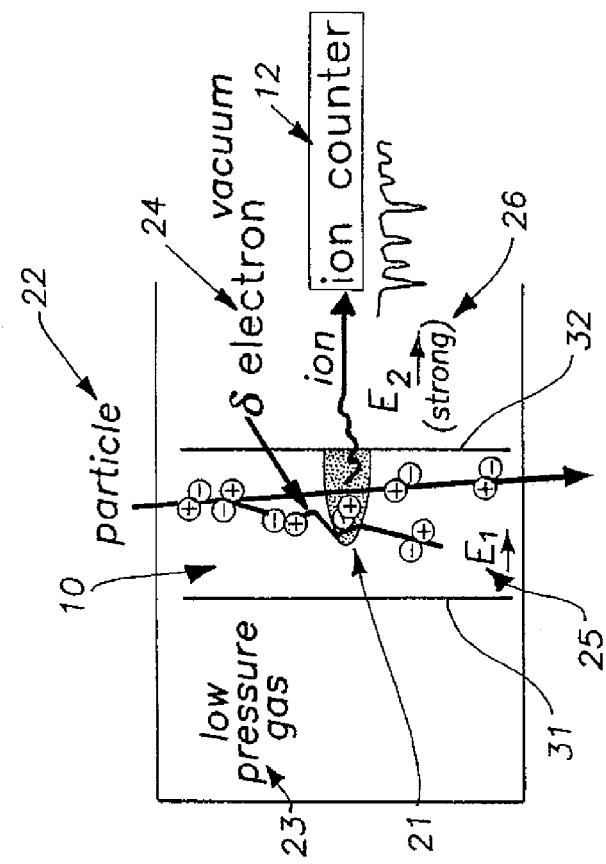
FIG. 2 is a conceptual diagram of the single ion counting method of nanodosimetry used in the present invention.

FIG. 2 is a conceptual diagram of the single ion counting method used in nanodosimeter 15, showing how a wall-less sensitive volume 21 can be formed in ionization chamber 10 filled with a low-pressure density gas 23 of approximately 1 Torr. An energetic ionizing particle 22 traversing ionization chamber 10 induces ionizations around its track, directly and through the mediation of δ electrons 24. Radiation-induced positive ions drift under a relatively weak electric field Esub1 25 of about 60–100 V/cm through a narrow aperture (about 1 mm diameter) at the bottom of the ionization chamber 10 toward the ion counter 12. Below the aperture the ions experience a much stronger electric field Esub2 26 of about 1500–2000 V/cm. The electric field strength and the diameter of the aperture define the lateral dimensions of a wall-less sensitive volume above the aperture from which the ions can be extracted with high efficiency. By changing the pressure inside the ionization chamber one can make further adjustments to the size of the sensitive volume, as will be evident to those skilled in the art. Since positive ions diffuse much less than electrons, sensitive volumes of about 0.1–4.0 nm tissue equivalent diameter and 2–40 nm tissue-equivalent length can be achieved with this method. By applying a time window during which ions are counted one can further define a subsection of the sensitive volume from which ions are counted.

Various cellular subsystems, most importantly water and DNA, can be simulated by using gases of different composition. As standard gas, one may use propane. As the low-energy ions do not undergo gas multiplication there are no limits on the gas 23 to be investigated.

Figure 3:
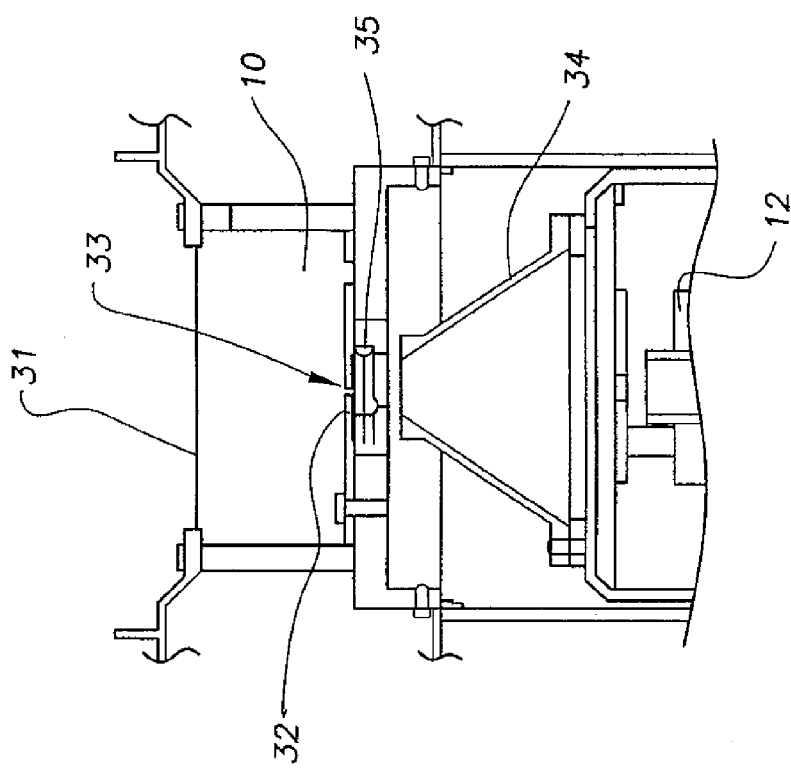
FIG. 3 is a cross-section diagram of the ionization cell and high vacuum chamber of the nanodosimeter of FIG. 1A.

FIG. 3 shows the actual design of the ionization chamber 10 and ion drift optics 35 of nanodosimeter 15. The upper electrode 31, which is at a positive potential of 300–500 Volts produces the drift field within the ionization chamber. A gold-plated aperture plate 32, which is at ground potential, contains an opening aperture 33 of about 1 mm diameter. Different aperture sizes may be used to adjust the width of the sensitive volume. Electrodes in ion drift optics 35 and a metal cone 34 generate the electric field below the aperture, which focus and accelerate the ions toward the cathode of the ion counter 12. The electrodes of the ion drift optics and metal cone are held at a negative potential of about 450 Volts, while the ion counter cathode is at a negative potential of about 7,000 to about 8,000 Volts.

Figure 4:
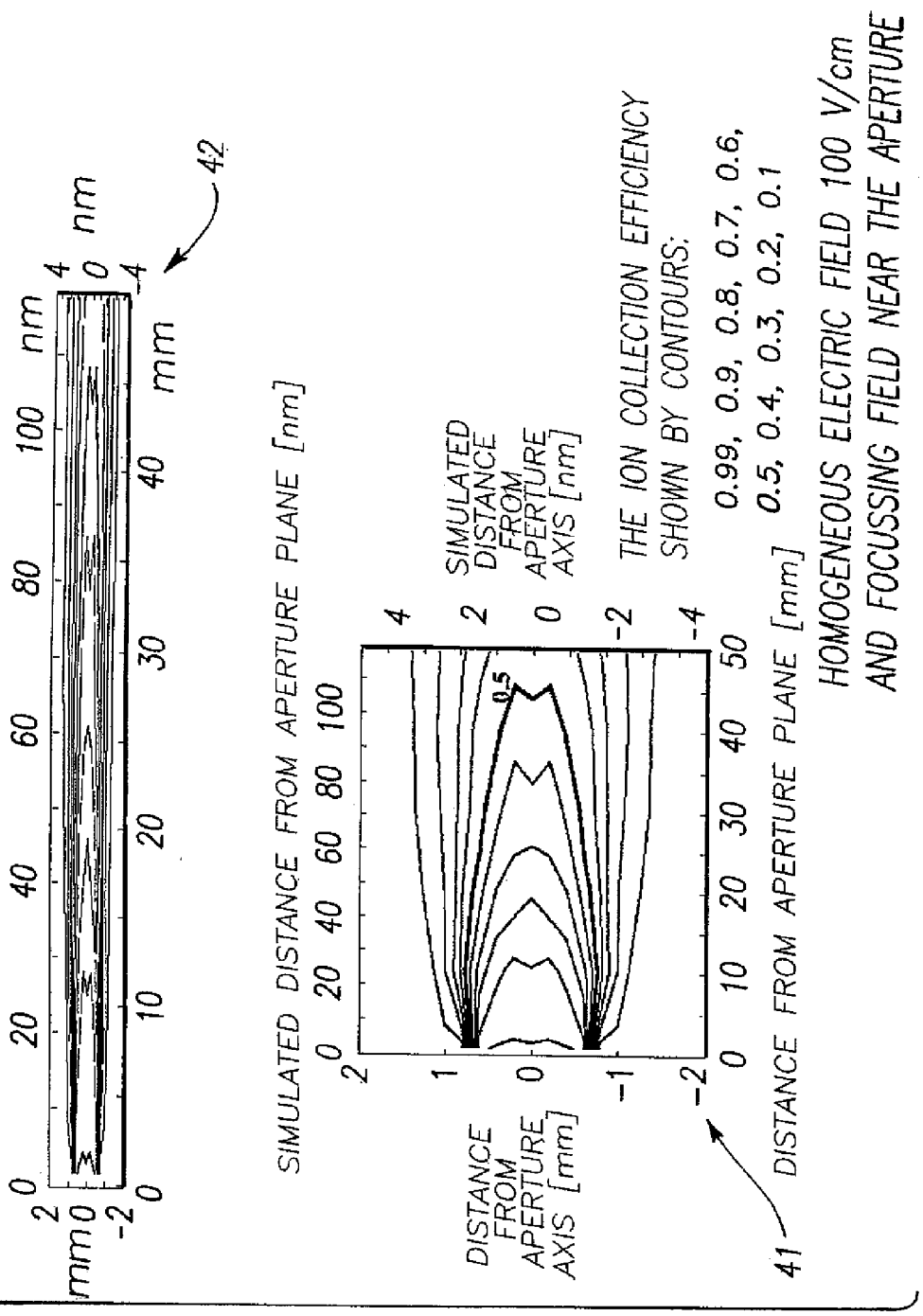
FIG. 4 is graph of calculated sensitive volume configurations as used in the present invention.

FIG. 4 shows calculated ion collection efficiency maps 41 and 42 of the sensitive volume for a field condition of temperature of 280 degrees K., a homogeneous electric field of 100 V/cm, and focusing field near the aperture 33, where map 41 is map 42 expanded for clarity. The maps are based on Monte Carlo studies of individual ion trajectories and measured ion diffusion parameters. The maps take into account actual electric field inhomogeneities. By changing the electric field strengths one can change the length and lateral diameter of the sensitive volume. In a further embodiment, the placement of additional electrodes in the vicinity of the sensitive volume and application of appropriate positive potentials enables the shape of the sensitive volume to be influenced. For example, the "candle-flame" shaped volume shown in FIG. 4 can be changed to a cylindrical volume by applying higher field strengths in the upper part of the volume.

Individual ions collected from the sensitive volume are counted with a vacuum-operated electron multiplier 12 of a type usually employed in mass spectroscopy. The model 14180HIG active film multiplier, SGE, or an equivalent, would be suitable. The counter generates fast signals from multiplied secondary electrons originating from the interaction of the accelerated ions with the multiplier cathode.

The ion counter 12 requires a vacuum in the order of $10^{-5}$ Torr. Maintaining this vacuum against the pressure of about 1 Torr in the ionization chamber 10 requires use of a differential pumping system consisting of two powerful turbo-molecular pumps. Pumps suitable for the purpose include the Varian Vacuum Technologies, Inc., models V250 for pump 14, and model V550 for pump 13, as shown in FIGS. 1A and 1B.

Figure 5:
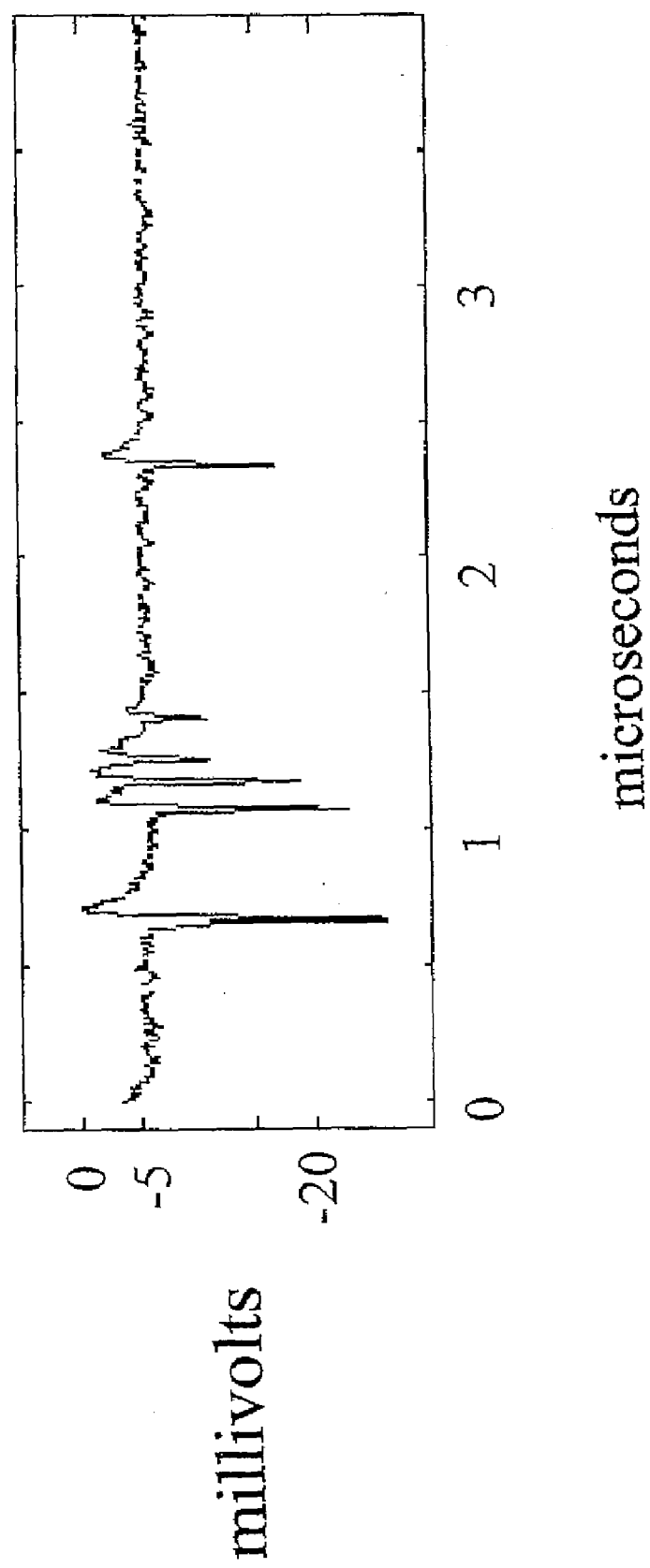
FIG. 5 is a graph of an example of a recorded ionization event using the nanodosimeter of FIG. 1A.

FIG. 5 shows an example of an ion trail spectrum produced by the nanodosimeter 15 of an alpha particle traversing the sensitive volume 21, where the x axis is in microseconds and the y axis is in millivolts measured by the ion counter 12.

A primary particle detection system which provides identification of single particle events must be added to the nanodosimeter 15. Furthermore, this provides for the measurement of the arrival time of the ions relative to the primary particle passage, thereby enabling the spatial localization of the ionization event along the principle symmetry axis of the sensitive volume. Due to the low mobility of the ions, the events are well separated in time. It has been shown that a spatial resolution of 1 nm tissue equivalent length can be achieved.

Figure 7:
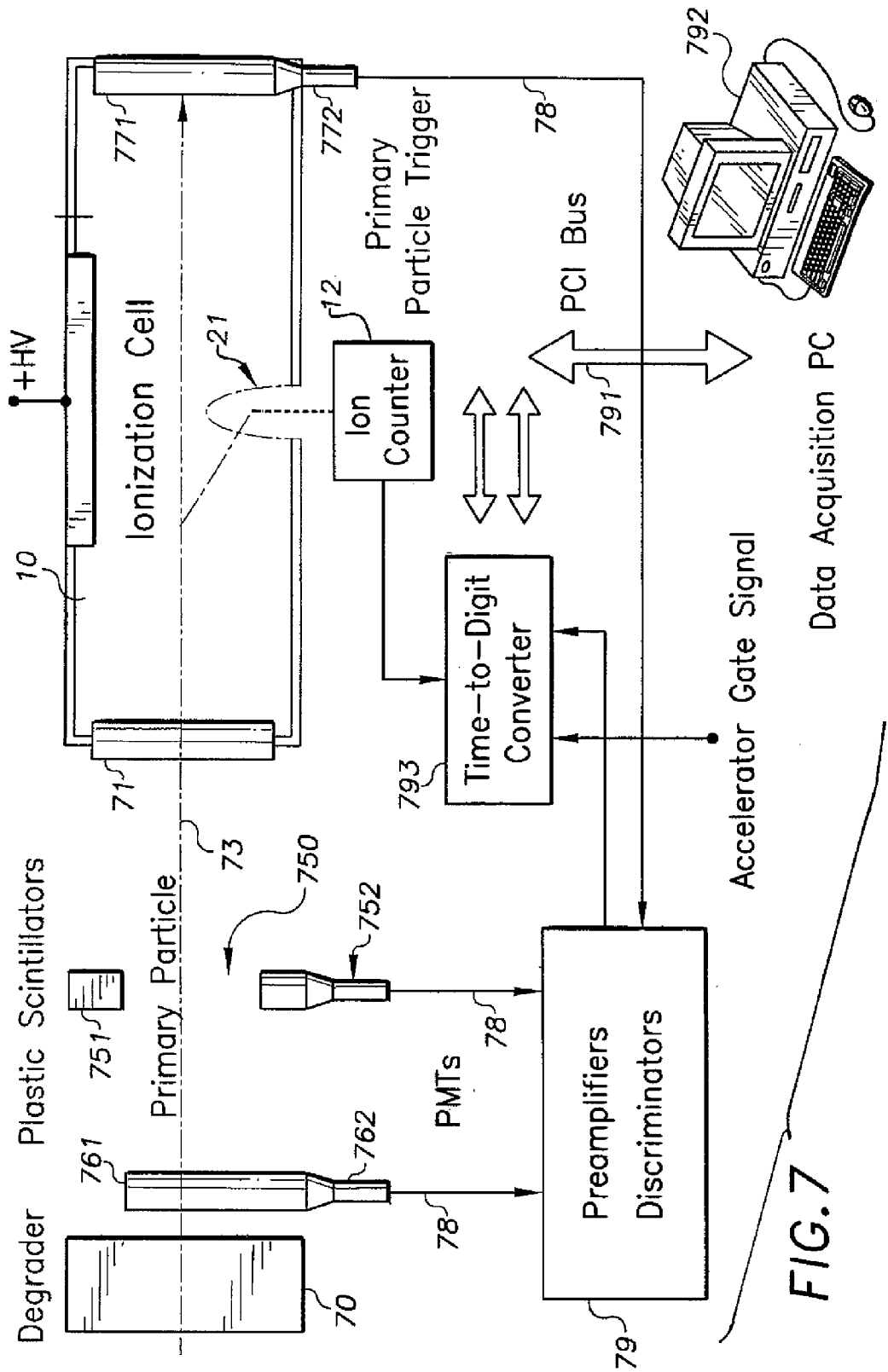
FIG. 7 is a schematic diagram of a nanodosimeter incorporating a particle tracking and data acquisition system according to another embodiment of the present invention.

FIG. 7 shows one embodiment of such a particle detection system, schematically diagraming how a detector is embedded into the triggering and data acquisition system. The implementation of a particle detection system tracking system enables the measurement of ionization clusters in the sensitive volume 21 for each primary particle event 73. The primary particle event 73 is reconstructed from the signals of particle sensitive detectors located in front and behind the sensitive volume. In this embodiment, three fast plastic scintillators (BC 408, Bicron), two of which are located at the front 761 and 751 and one at the rear end 771 of the ionization chamber 10, register primary particles that enter the ionization chamber 10 and pass through it. The downstream front-end scintillator 751 contains an opening 750 of a specified shape and is used in anticoincidence to the up-stream front-end scintillator 751 to select the cross-sectional area of particle detection. Photomultiplier tubes (PMTs) 762, 752 and 772 register the light signals provided by the scintillators. The PMT signals 78 are then processed by fast front-end electronics (preamplifiers and discriminators) 79 and sent to data acquisition boards (PCI 6602, PCI6023E, National Instruments) via an interface board, which provides fast NIM signal conversion to TTL/CMOS signals. The data acquisition boards 793 perform time-to-digit conversion of the arrival times of each signal and amplitude-to-digit conversion of the rear scintillator signal, which contains information about the energy of the primary ionizing particle. The digital data are sent along a PCI bus 791 to a dedicated data acquisition PC 792, where they are processed, displayed and stored.

In this embodiment, the data acquisition process can also be synchronized to gate signals provided by the external radiation source, for example, a synchrotron which delivers particles in form of spills with a complex time structure.

Figure 8:
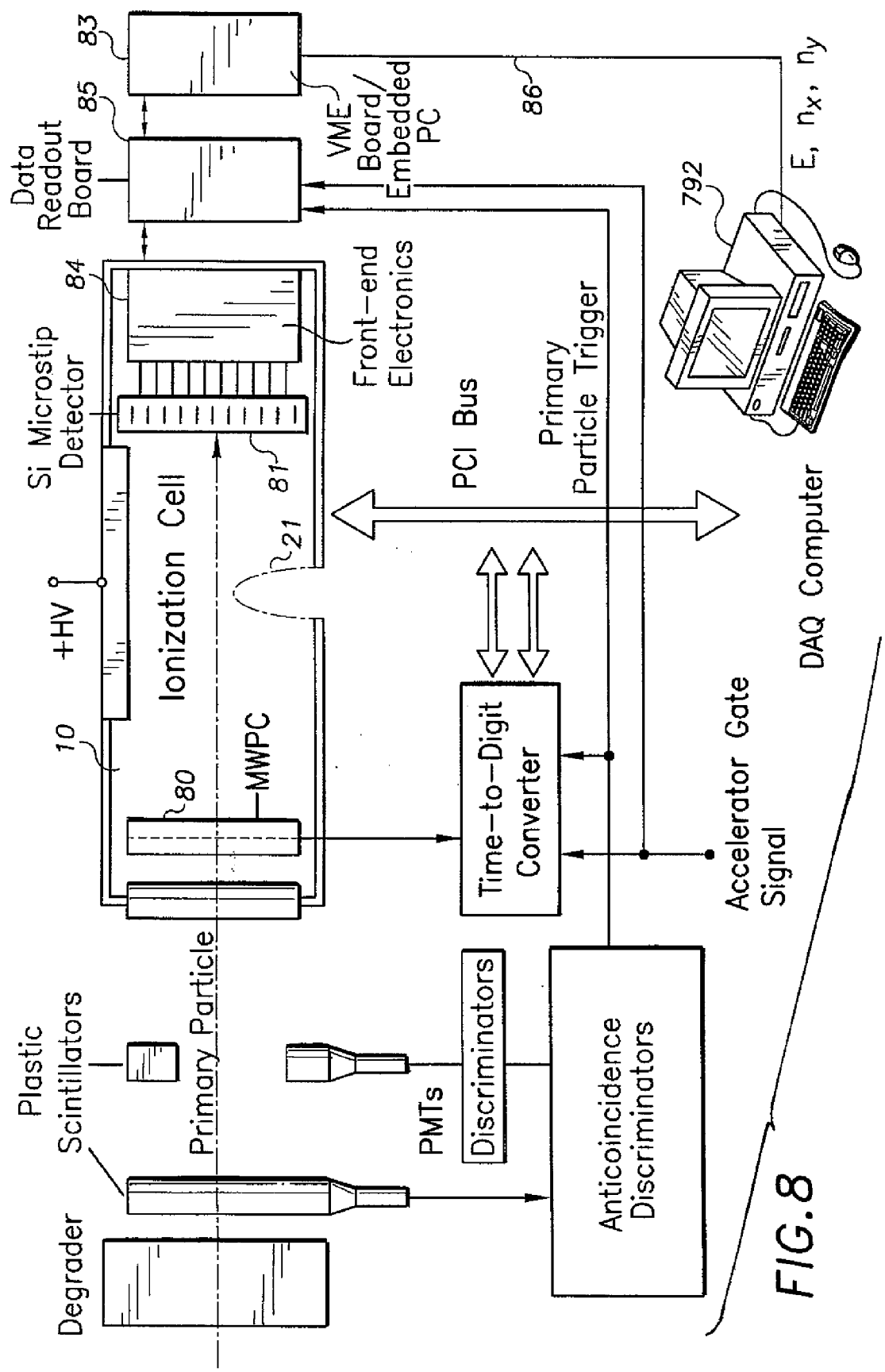
FIG. 8 is a schematic diagram of a nanodosimeter incorporating a particle tracking and data acquisition system according to further embodiment of the present invention.

FIG. 8 shows a further embodiment of a position-sensitive triggering system. For clarity, the ion counter 12 is not shown in this figure. This embodiment uses, within the ionization chamber 10, a multiwire proportional chamber (MWPC) 80 as used in high-energy physics experiments, upstream of the sensitive volume and a double-sided silicon microstrip detector (e.g., S6935, Hamamatsu Corp.) 81 downstream of the sensitive volume. In this configuration, the distance between the sensitive volume 21 and the MWPC 80 is in the order of 8 cm, whereas it is only about 3 cm between the sensitive volume 21 and the microstrip detector 81, With this configuration, a spatial resolution of the track position in the plane of the sensitive volume is in the order of 100 μm (0.1 mm). It has been known from high energy physics experiments that silicon microstrip detectors can be used for precise tracking of charged particles, but have not been implemented in nanodosimetry.

Very large statistical samples must be accumulated with the nanodosimeter to detect rare high-order ionization events. Readout schemes for on-line reduction of such samples, utilizing a digital signal processor located on front-end boards 84 and 85 and embedded computer networks 83, as shown in FIG. 8, are now widely used in high-energy physics experiments, but have not been implemented in nanodosimetry. Using the system shown in FIG. 8, signals 86 comprising information on energy, and multi-dimensional position of the primary particle can be passed to the DAQ computer 792 for processing.

Figure 6:
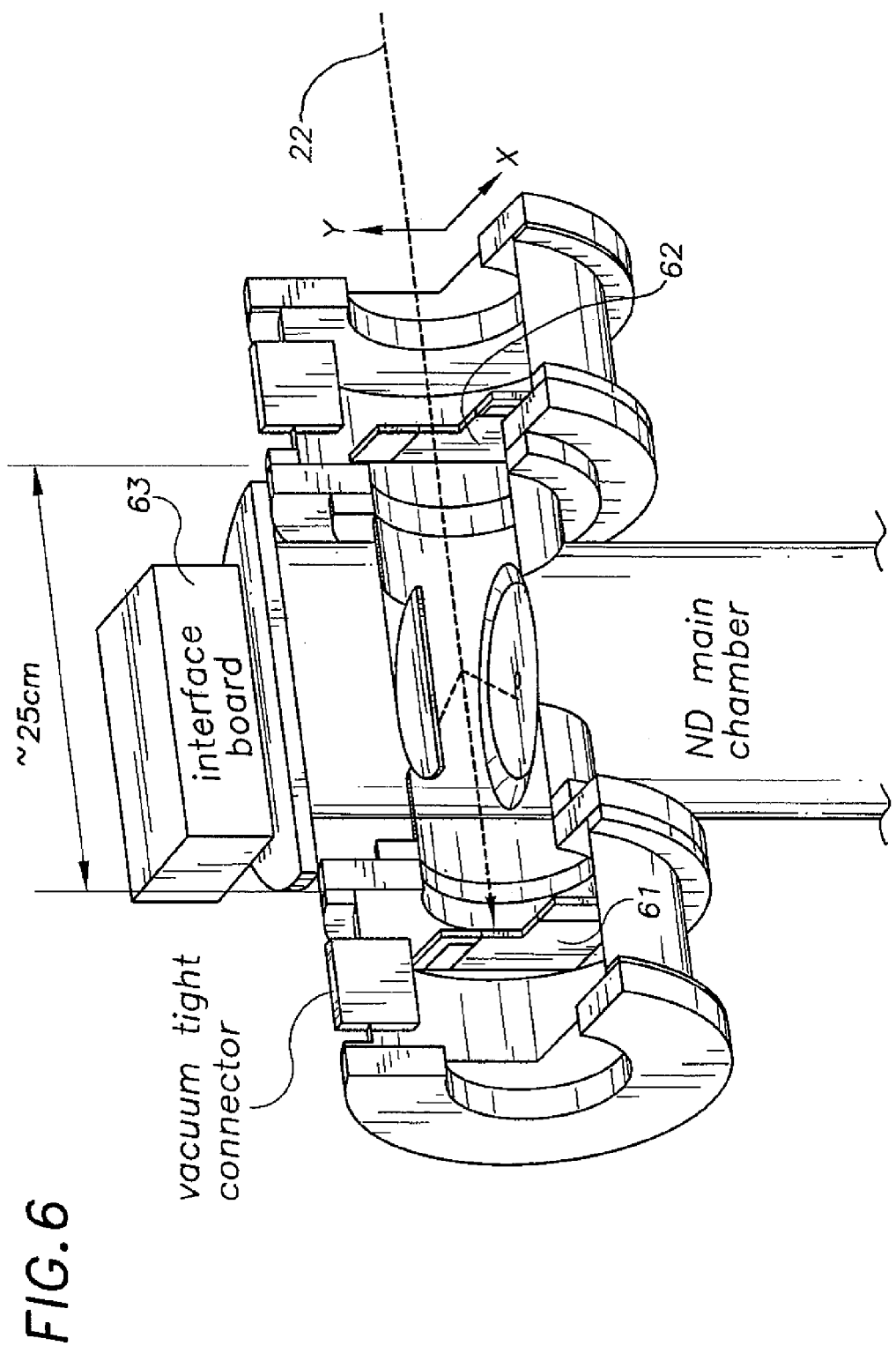
FIG. 6 is a schematic diagram of a nanodosimeter incorporating a multi-axis particle tracking system according to one embodiment of the present invention.

FIG. 6 shows a further embodiment of a position-sensitive triggering and energy measurement system integrated into the nanodosimeter 15. This embodiment comprises two silicon strip detector modules 61 and 62 that convey the X- and Y-position of the particle 22 relative to the sensitive volume with a resolution that is determined by the strip pitch, and which is usually better than 0.2 mm. In addition, the silicon strip detectors can measure the energy deposited by each primary particle across the depletion layer of the silicon crystals, thus providing information about the energy and LET of the primary particle over a wide range of particle energies. Using the system shown in FIG. 6, signals comprising information on energy, and multi-dimensional position of the primary particle can be passed to the DAQ computer through interface board 63 for processing.

Figure 11A:
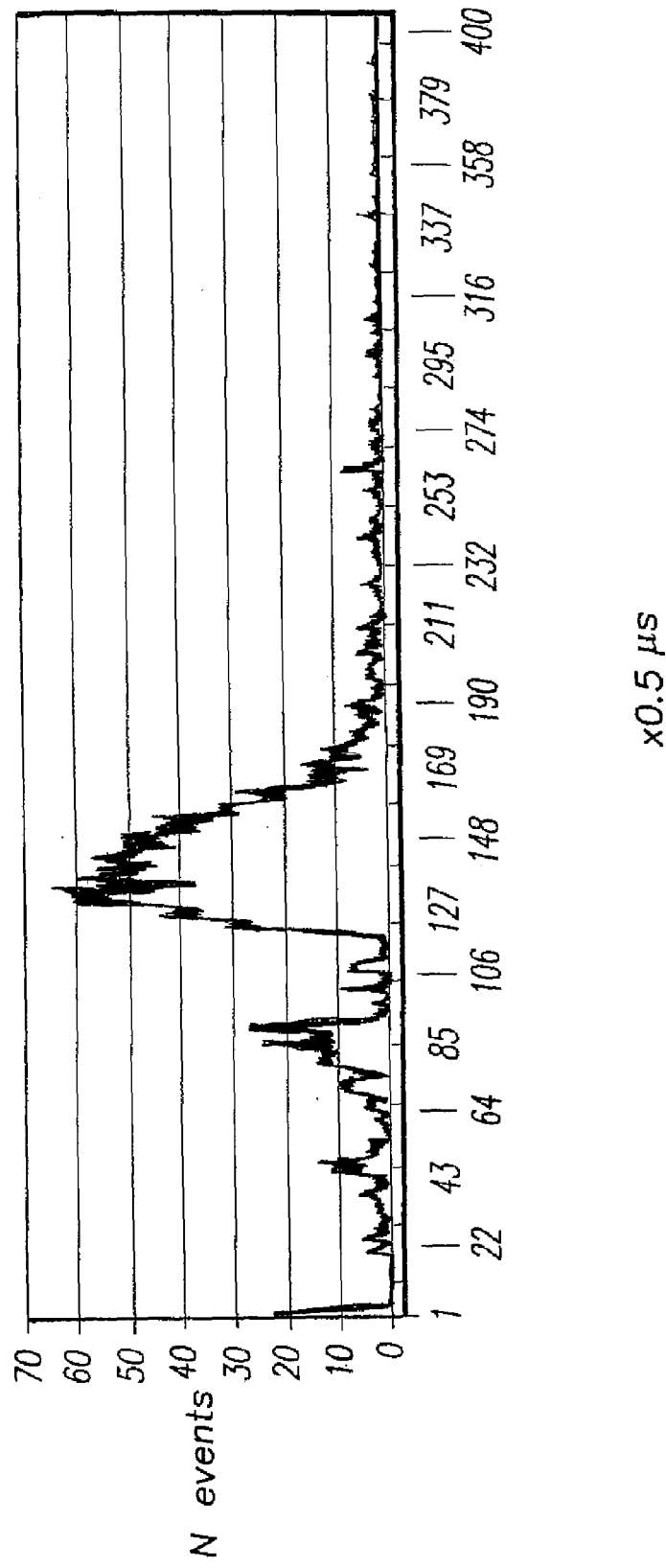
FIG. 11 is a graph of an example of a frequency distribution of recorded events by strip number, according to one embodiment of the present invention.

FIG. 11 shows, as an example of the position-sensitive system performance of the silicon strip embodiment, a hit-strip distribution 110 providing particle position information, and the time-over-threshold distribution 111 representing the energy deposition distribution of a 40 MeV proton beam collimated to 1.5-mm width. The hit-strip distribution clearly demonstrates the high spatial resolution of particle coordinate measurements.

In this embodiment, the front silicon-strip detector module comprises two single-sided silicon micro-strip detectors with orthogonal strip orientation, and the back detecor module comprises one double-sided silicon micro-strip detector located behind the sensitive volume. This arrangement of detectors provides information about the primary particle track from the strip-hit information as well as the particle's energy over a wide range of energies. This allows quantifying the nanodosimeter information as a function of the primary particle energy and position.

Figure 13:
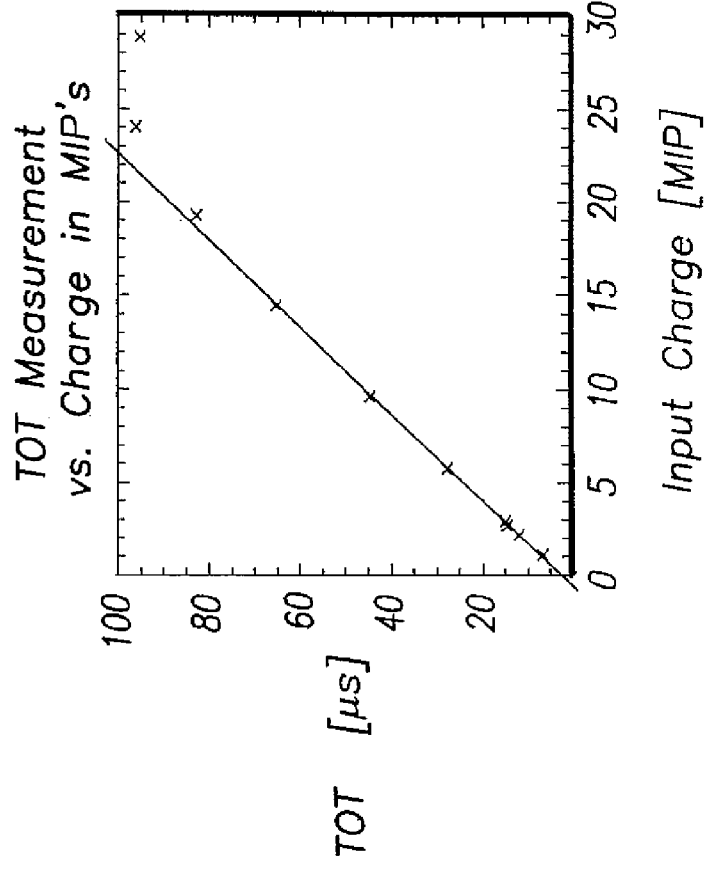
FIG. 13 is a graph showing calibration of the Time-Over-Threshold ASIC in one embodiment of the particle tracking system, in which TOT is a function of the input charge in multiples of the charge deposited by a minimum ionizing particle (MIP)

For the readout of the fast silicon detector signals, it is preferable to use a low-noise, low-power front end ASIC, such as was developed for the GLAST mission, in which the input charge is measured through the pulse width, i.e., as a time-over-threshold (TOT) signal, over a large dynamic range. An example of the measured electronic calibration of the chip TOT vs. input charge (in units of charge deposited by a minimum ionizing particles, MIP) is shown in FIG. 13.

Figure 14:
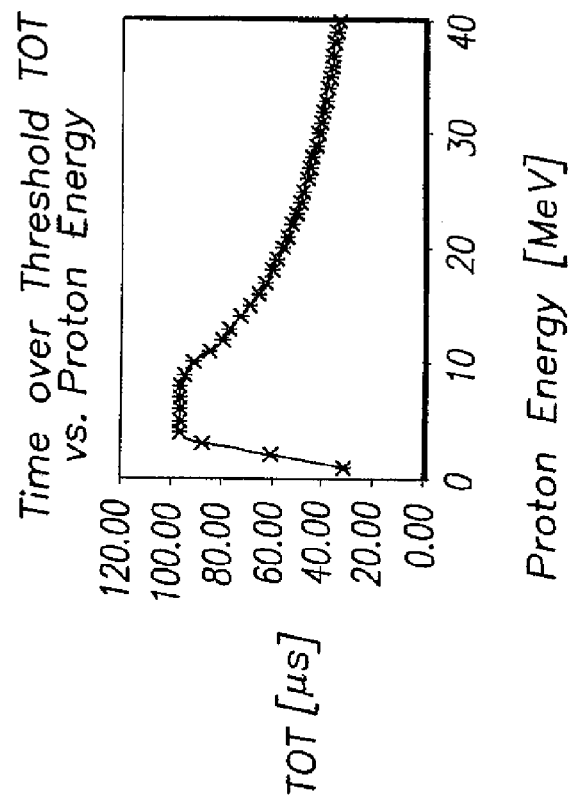
FIG. 14 is a graph showing Predicted Time-over-Threshold (TOT) signal in one embodiment of the particle tracking system, as a function of the proton energy.

FIG. 14 shows an expected TOT signal vs. the energy of the primary protons incident on a silicon micro-strip detector using the three detector (two single-sided silicon microstrip/one double-sided silicon micro-strip) embodiment. The method of determining the energy of the proton from its specific energy deposition using the TOT signal of a single detector is expected to be viable for proton energies above about 10 MeV and below about 3 MeV. The proton energy can be measured uniquely at energies above 10 MeV and below 3 MeV. However, in the energy range of about 3–15 MeV, protons deposit a significant fraction of their energy in the silicon detector, so that the TOT signal of at least one of the three detectors will be within the measurable range, and thus will provide sufficient information to reconstruct the energy of the particle passing the ionization chamber. At higher energies, i.e., above about 15 MeV, the TOT signal is a relatively shallow function of incident proton energy, but for these energies all three detectors will provide a measurement, thereby reducing the measurement uncertainty.

Monte Carlo calculations with low energy proton beams can be used to test a relationship such as shown in FIG. 14, and to determine the resolution of this energy determination method. Since multiple scattering of protons in the low-pressure gas volume of the detector is minimal, the position resolution is mainly determined by the pitch of the microstrip detectors.

Each of the described embodiments for a position-sensitive tracking system requires a data acquisition system (DAQ), that receives input from the ion counter 12, primary particle trigger signals either from the built-in particle tracking system or from scintillators, an accelerator start signal when used with a synchrotron accelerator, and position and energy-deposition data from the particle-tracking system. The DAQ system preferably uses fast PCI technology which receives and sends data from and to an interface board 63 with reference to FIG. 6. The DAQ system coordinates the readout of all data signals and performs online and offline data analysis.

In another embodiment, the present invention is a method of correlating the response of the nanodosimeter with the presence or extent of damage to a nucleic acid within a sample. In a preferred embodiment, the nucleic acid containing sample is an in-vitro solution of plasmid DNA. In other embodiments, the DNA is viral, chromosomal, or from a minichromosome.

Figure 12:
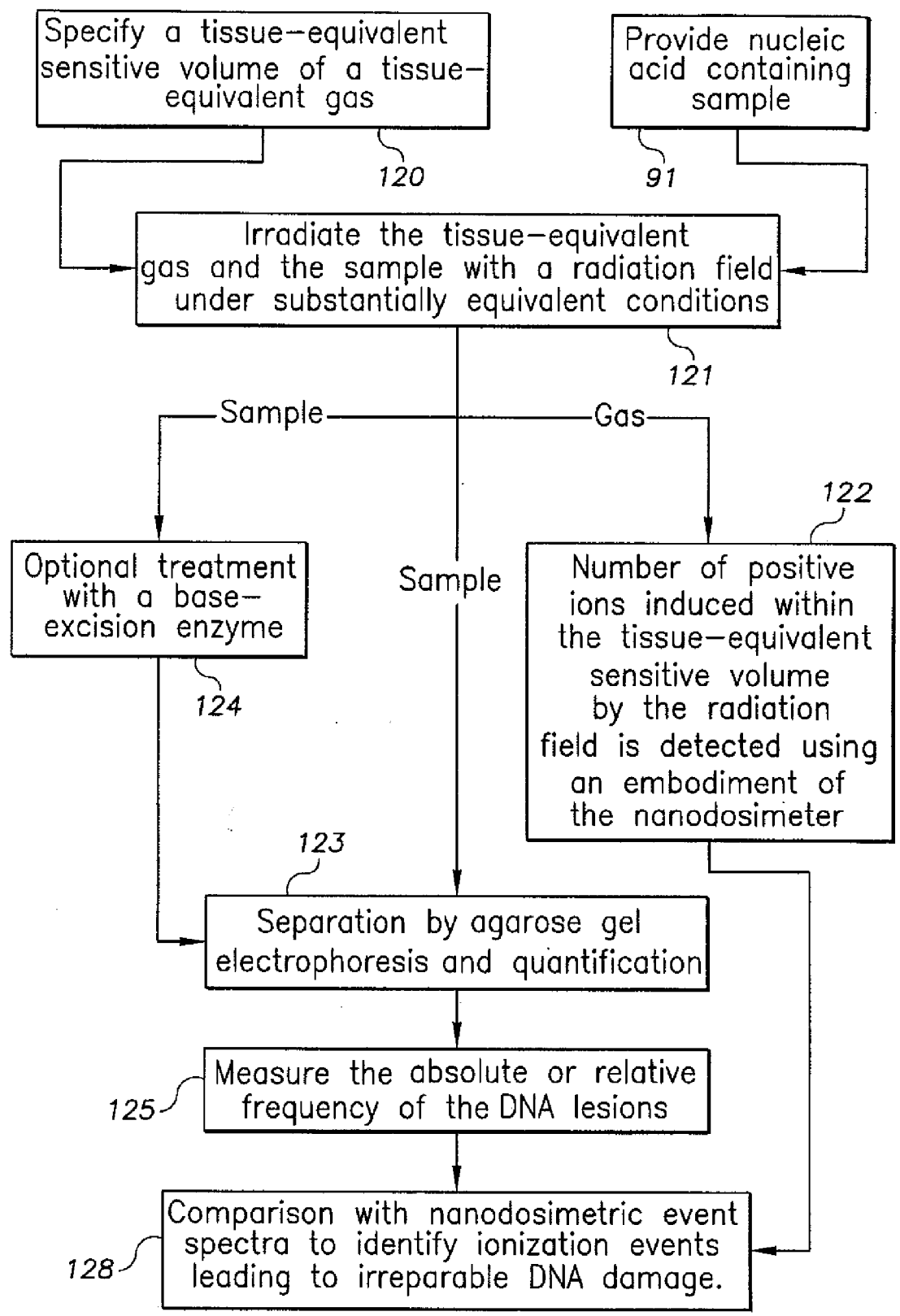
FIG. 12 is a flow chart show the method of calibration of the nanodosimeter of FIG. 1A, comprising one of the embodiments of the particle tracking system, to biological damage according to the present invention.

With reference to FIG. 12, the method typically includes specifying a tissue-equivalent sensitive volume of a tissue-equivalent gas 120. The tissue equivalent sensitive volume is typically selected to model a particular tissue equivalent volume, such as a discrete length of a double stranded DNA. In the current embodiment, the typical sensitive volume can be specified to be between about 0.1 nm and about 4 nm tissue-equivalent in diameter and between about 2 nm and up to about 40 nm in tissue-equivalent length. In one embodiment, the sensitive volume is the tissue-equivalent sensitive volume is between about 0.2 $nm^3$ and about 500 $nm^3$. Preferably, the tissue-equivalent sensitive volume is between about 20 $nm^3$ and about 100 $mm^3$. The optimal sensitive volume size and gas composition is that which gives the highest degree of correlation between measured DNA lesions and those predicted from nanodosimetric data.

The method further comprises irradiating the tissue-equivalent gas and the sample with a radiation field 121. Preferably, the nucleic acid containing sample is exposed to a substantially equivalent quality of radiation that is measured by the nanodosimeter 15. The plasmid is typically dissolved in an aqueous solution that simulates the cellular environment such as, for example, a solution including glycerol and a buffer. This is done to reproduce the diffusion distance of OH radicals with a living cell. Preferably, the sample is irradiated with a range of doses in order to establish a dose-response relationship. Preferably, the DNA concentration and range of irradiation doses are selected such that each plasmid will, on average, contain about one DNA damage of variable complexity. For example, irradiation of a plasmid sample having a concentration of 1 mg/ml with a dose of about 10 Gy of low-LET radiation will result, on average, in one single stranded break for each plasmid.

In a preferred embodiment, the number of positive ions induced within the tissue-equivalent sensitive volume by the radiation field is detected 122 using an embodiment of the nanodosimeter with particle tracking and energy measuring system described herein.

The frequency distribution of damages of variable complexity to the nucleic acid within the sample is compared with the frequency distribution of variable clusters of positive ions induced within the tissue-equivalent sensitive volume. By damage of variable complexity we refer to base damages (B) or strand breaks (S) occurring on either strand of the DNA and ranging from a single damage site to multiple combinations of these damages.

One embodiment of the calibration assay is illustrated in FIG. 10. In this embodiment, each sample includes a thin film of an aqueous solution of plasmid DNA 91. The sample is exposed to the same radiation quality as the nanodosimeter. The irradiated plasmid sample is optionally treated with a base-excision enzyme 124 such as endonuclease formamidopyrimidine-DNA N-glycosylase (FPG) or endonuclease III. These enzymes transform base damages in the DNA of irradiated plasmids into strand breaks. Damages that contain at least one strand break located in complementary strands in close proximity to each other are converted from a closed supercoiled form into a linear form. Damages that contain at least one strand break on only one strand will be transformed into a relaxed open circle.

The different physical states of plasmids (supercoiled, open circle, linear) are separated by agarose gel electrophoresis and quantified after staining with a fluorescent dye 123. The calibration assay allows one to distinguish and to measure 125 the absolute or relative frequency of the following types of DNA lesions: lesions that contain at least one strand break on one strand but not on the other strand (S0); lesions that contain at least one base damage on one strand but not on the other strand (B0); lesions that contain at least one strand break on complementary strands (SS); lesions that contain at least one base damage on complementary strands (BB); and lesions that contain at least one base damage on one strand and at least one strand break on the other strand (SB).

Figure 9A:
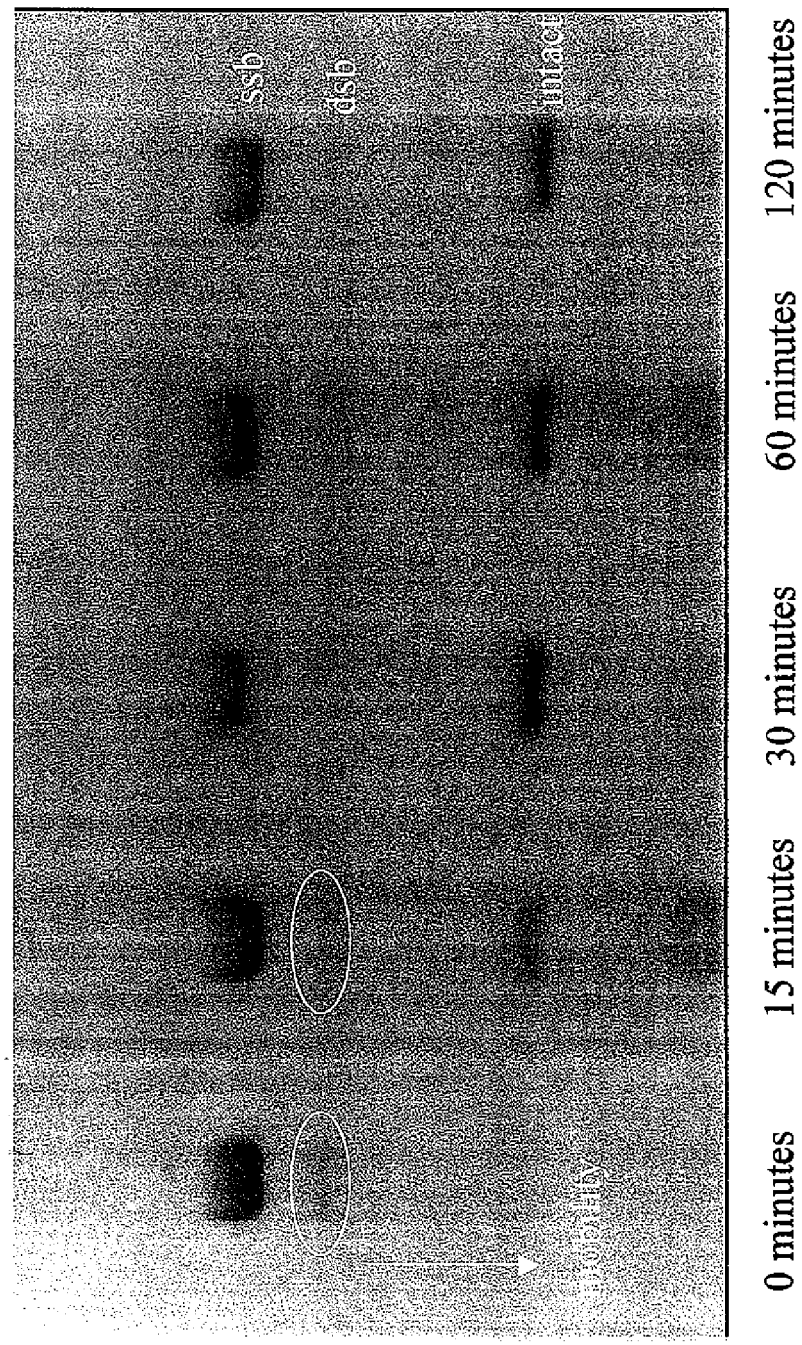
FIG. 9 is a pictorial flow chart representing a calibration method according to one embodiment of the present invention.
Figure 9B:
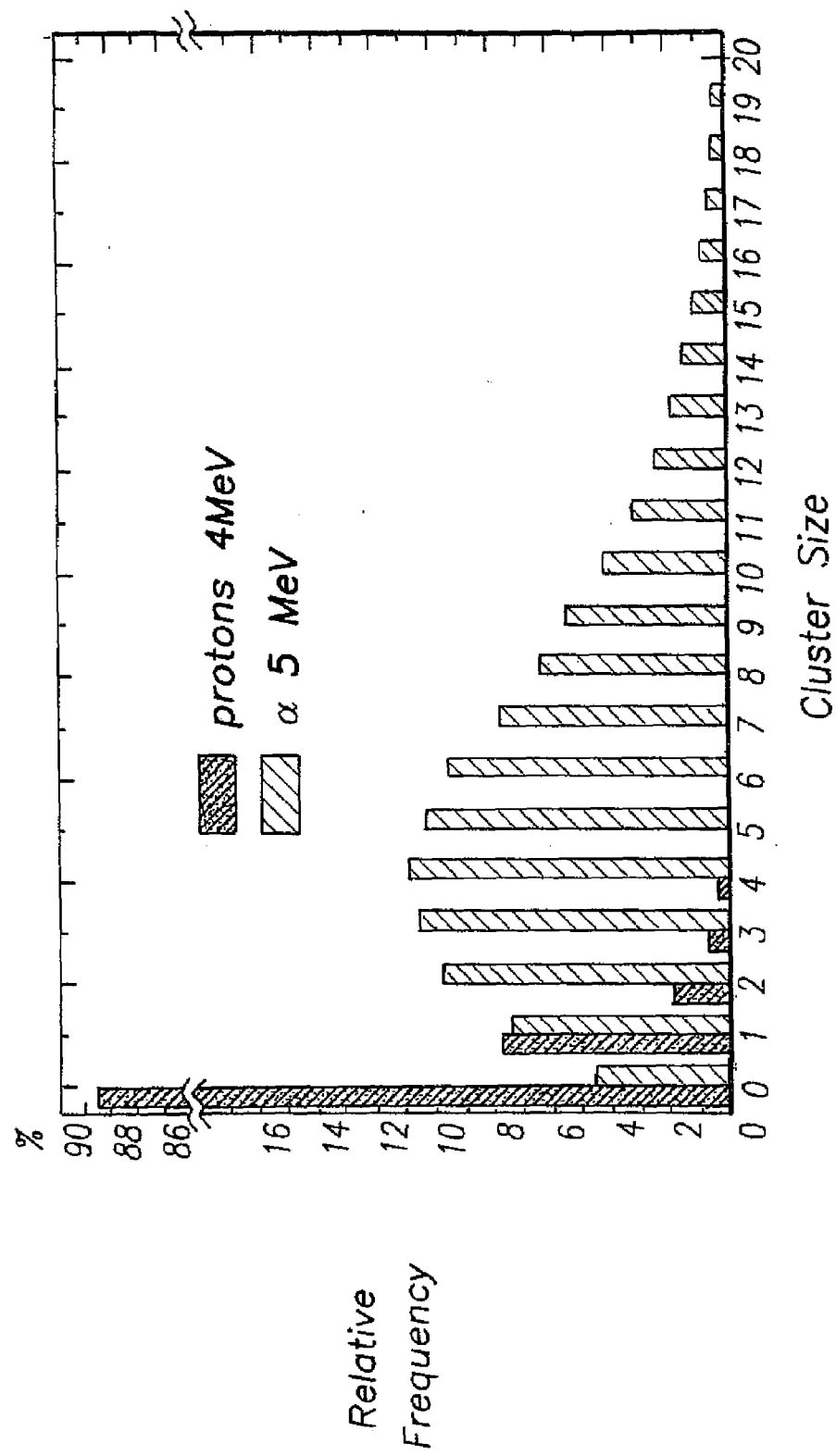

According to another embodiment of the calibration assay shown in FIG. 9, thin films of supercoiled plasmids conferring antibotic resistance and a reporter gene such as β-galactosidase are exposed to the same radiation quality as the detector. Plasmids that contain DNA damages of variable complexity are separated from each other and undamaged plasmids by gel electrophoresis. After separation, the damaged plasmids are extracted from the gel and incubated with a mammalian repair extract 126 or a *Xenopus laevis* oocyte extract for several hours to allow DNA damage to be repaired. After incubation, the plasmids are transfected into antibiotic-sensitive bacterial host cells 127 and the bacteria are grown in the presence of the antibiotic to select for successfully transformed bacteria. The reporter gene of the plasmid is used to detect misrepaired DNA damage. Cells containing the intact gene produce a colored dye when incubated with the indicator. This compound is colorless, unless cleaved by β-galactosidase. Colonies that contain a non-functional reporter gene are not colored.

In this way, one can measure the fraction of unrepaired or misrepaired damage in a given amount of DNA for different radiation qualities, and by comparison with nanodosimetric event spectra 128, identify ionization events leading to mis-reparable DNA damage.

In another aspect of the invention, the probability that a single ionization event proximal to a nucleic acid will result in a single strand break or a base damage is determined by the calibration assay. From this, the frequency of the each type of nucleic acid lesion is calculated for ionization clusters of a given size. The calculated frequency of particular nucleic acid lesions for ionization clusters of a discrete size is compared with the frequency distribution of ionization clusters measured with the nanodosimeter to predict the absolute and relative frequency of each type of nucleic acid lesion.

Although the present invention has been described in considerable detail with reference to certain preferred versions thereof, other versions are possible. For example, in alternative embodiments the invention includes a method for determining a dose of radiation for radiation therapy using the procedure, a method of predicting death or mutation in a living cell, a method of modeling the effect of radiation in a living cell, a method evaluating radiation risk for manned space missions, and assessment of radiation exposure of aircraft crew and frequent flyers. The present invention has many potential applications to various areas including but not limited to planning and optimizing of radiation therapy with charged particles, design and evaluation of radiation shielding, radiation protection, monitoring of occupational and other terrestrial radiation environments. Therefore, the scope of the appended claims should not be limited to the description of the preferred versions described herein.

One particularly important and novel application of the nanodosimeter is the determination of W, the average energy required to produce an ion pair in gases as a function of particle energy. More accurately, W is the quotient of E and N, where N is the mean number of ion pairs formed when the initial kinetic energy, E, of a charged particle is completely dissipated in the gas. While W is known with good accuracy only for a limited number of particle types and energies, accurate knowledge of the energy dependence of W is highly desirable both for basic understanding of dosimetric theory and for application in medical dosimetry. For example, accurate determination of the dose delivered in neutron or proton therapy requires mapping of the energy dependence of W for protons and heavy recoil ions over a wide range of energies with an accuracy of better than 2%. This goal has currently not been accomplished.

The nanodosimeter can be used to measure the differential value, w(E), of the mean energy necessary to produce an ion pair relative to a known value $W(E_{ref})$ at a reference energy $E_{ref}$. The differential value w is defined as the quotient of dE by dN, where dE is the mean energy lost by a charged particle of energy E traversing a thin gas layer of thickness dx, and dN is the mean number of ion pairs formed when dE is dissipated in the gas. Alternatively, one may express w as a function of the stopping power S(E)=dE/dx of the gas, which is usually known with good accuracy:

$$w(E)=S(E)/dN \cdot dx$$

With the particle tracking system of the nanodosimeter one can select primary particles with the reference energy $E_{ref}$ and a given energy E that pass the sensitive volume of the nanodosimeter at a given distance y from the aperture. The ratio of $N_1(E_{ref})$ and $N_1(E)$, the average number of nanodosimetric ion counts for primary particle energies $E_{ref}$ and E, can then be used as a good approximation for the ratio of $dN(E_{ref})$ and dN(E), thus $$w(E)/w(E_{ref})=S(E)/S(E_{ref})N_1(E_{ref})/N_1(E)$$

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A nanodosimeter device for detecting positive ions induced in a sensitive gas volume by a radiation field of primary particles, comprising:
   an ionization chamber filled with a low-pressure density gas including the sensitive gas volume to be irradiated by the radiation field of primary particles, the ionization chamber having an aperture opening;
   an ion counter system connected to the ionization chamber for detecting the positive ions, the ion counter system having an ion counter in communication with the aperture opening;
   a particle tracking system having a position-sensitive detector for detecting the primary particles passing through the sensitive gas volume; and
   a data acquisition system that receives and correlates data from the ion counter system and the particle tracking system.

2. The nanodosimeter of claim 1, wherein the particle tracking system is capable of multi-axis position-sensitive detection of the primary particles passing through the sensitive gas volume.

3. The nanodosimeter of claim 1, wherein the particle tracking system further comprises an energy measurement system for measuring the energy of the primary particles passing through the sensitive gas volume.

4. The nanodosimeter of claim 1, further comprising a radiation source in communication with the ionization cell chamber, for injection of the radiation field of primary particles into the ionization cell chamber.

5. The nanodosimeter of claim 4, wherein the radiation source is a source of a particles.

6. The nanodosimeter of claim 4, wherein the radiation source is a source of ionizing particles.

7. The nanodosimeter of claim 4 wherein the radiation source is an accelerator.

8. The nanodosimeter of claim 7, wherein the accelerator comprises a synchrotron.

9. The nanodosimeter of claim 1, wherein the position-sensitive detector comprises a plurality of scintillators and photomultiplier tubes.

10. The nanodosimeter of claim 1, wherein the position-sensitive detector comprises a silicon microstrip and a multiwire proportional chamber.

11. The nanodosimeter of claim 1, wherein the position-sensitive detector comprises a plurality of silicon microstrips.

12. The nanodosimeter of claim 1, wherein the sensitive gas volume comprises propane.

13. A method for measuring positive ions induced by a radiation field of primary particles, comprising the steps of:
   providing a tissue-equivalent gas;
   determining a tissue-equivalent sensitive gas volume of the tissue-equivalent gas;
   irradiating the sensitive gas volume with the radiation field;
   detecting the positive ions induced by the radiation field;
   tracking the primary particles that pass through the sensitive gas volume; and
   correlating data regarding the positive ions and primary particles.

14. The method of claim 13, further comprising the step of scaling the data from the nanodosimeter for the sensitive gas volume to a DNA-size volume.

15. The method of claim 13, further comprising the steps of:
   selecting primary particles using the particle tracking system with a reference energy $E_{ref}$ and a given energy E that pass the sensitive gas volume;
   calculating a ratio of $N_1(E_{ref})$ and $N_1(E)$, which are the average number of nanodosimeter ion counts for primary particle energies $E_{ref}$ and E, respectively;
   using the ratio of $N_1(E_{ref})$ and $N_1(E)$ as an approximation for the ratio of $dN(E_{ref})$ and $dN(E)$; and
   computing the differential value w(E) according to the formula $$w(E)/w(E_{ref}) = S(E)/S(E_{ref}) N_1(E_{ref})/N_1(E).$$

16. A method for calibrating radiation exposure from a first radiation field with the presence or extent of damage to a nucleic acid within a sample, the method comprising the steps of:
   providing a tissue-equivalent gas;
   determining a tissue-equivalent sensitive gas volume of the tissue-equivalent gas;
   irradiating the tissue-equivalent gas and the sample with the first radiation field;
   calculating the number of positive ions induced within the sensitive gas volume by the first radiation field;
   detecting the presence or extent of damage to the nucleic acid within the sample following irradiation with a second radiation field; and
   comparing and correlating the extent of damage to the nucleic acid within the sample with the calculated number of positive ions induced by the first radiation field.

17. The method of claim 16, wherein the second radiation field is equal to the first radiation field.

* * * * *

UNITED STATES PATENT AND TRADEMARK OFFICE
CERTIFICATE OF CORRECTION

| | |
|---|---|
| PATENT NO. | : 7,081,619 B2 |
| APPLICATION NO. | : 10/894873 |
| DATED | : July 25, 2006 |
| INVENTOR(S) | : Bashkirov et al. |

It is certified that error appears in the above-identified patent and that said Letters Patent is hereby corrected as shown below:

On the first page, column 1 (Inventors), line 3, please delete "Sergei" and insert -- Sergi --, therefor.

On the first page, column 2 (Other Publications), line 1, please delete "Shehemelinin" and insert -- Shchemelinin--, therefor.

On the first page, column 2 (Other Publications), line 1, please delete "Jonisation" and insert -- Ionisation--, therefor.

On the first page, column 2 (Abstract), line 14, please delete "position sensitive" and insert -- position-sensitive --, therefor.

At column 1, line 13, please delete "Detection." and insert -- Detection, --, therefor.

At column 2, line 49, please delete "run" and insert -- nm --, therefor.

At column 3, line 30, please delete "system;" and insert -- system, --, therefor.

At column 3, line 42, after "particles" insert --. --.

At column 4, line 60, please delete "low pressure" and insert -- low-pressure --, therefor.

At column 5, line 9, please delete "Esub1" and insert -- $E_1$ --, therefor.

At column 5, line 12, please delete "Esub2" and insert -- $E_2$ --, therefor.

At column 5, line 21, please delete "tissue equivalent" and insert --tissue-equivalent--, therefor.

At column 5, line 48 (approx.), please delete "280 degrees" and insert -- 280°--, therefor.

UNITED STATES PATENT AND TRADEMARK OFFICE
CERTIFICATE OF CORRECTION

| | | |
|---|---|---|
| PATENT NO. | : 7,081,619 B2 | |
| APPLICATION NO. | : 10/894873 | |
| DATED | : July 25, 2006 | |
| INVENTOR(S) | : Bashkirov et al. | |

It is certified that error appears in the above-identified patent and that said Letters Patent is hereby corrected as shown below:

At column 6, line 24, please delete "tissue equivalent" and insert --tissue-equivalent--, therefor.

At column 7, line 46, please delete "detecor" and insert -- detector --, therefor.

At column 8, line 42, please delete "tissue equivalent" and insert -- tissue-equivalent --, therefor.

At column 8, line 43, please delete "tissue equivalent" and insert --tissue-equivalent--, therefor.

At column 8, line 52, please delete "mm$^3$." And insert -- nm$^3$. --, therefor.

At column 9, line 49, please delete "antibotic" and insert -- antibiotic--, therefor.

At column 10, line 49, please delete "W(E$_{ref}$)" and insert -- w(E$_{ref}$) --, therefor.

At column 10, line 58, please delete "dN•dx" and insert -- dNdx --, therefor.

At column 10, line 67, after "$N_1(E)$" insert -- . --.

At column 11, line 53, in Claim 5, after "of" delete "a" and insert -- α --, therefor.

At column 11, line 56, in Claim 7, after "claim 4" insert -- , --.

UNITED STATES PATENT AND TRADEMARK OFFICE
CERTIFICATE OF CORRECTION

PATENT NO.         : 7,081,619 B2
APPLICATION NO.    : 10/894873
DATED              : July 25, 2006
INVENTOR(S)        : Bashkirov et al.

It is certified that error appears in the above-identified patent and that said Letters Patent is hereby corrected as shown below:

At column 12, line 38 in Claim 15, delete "$N_I(E_{ref})/N_I(E)$." and insert

-- $N_1(E_{ref})/N_1(E)$. --, therefor.

Signed and Sealed this

Tenth Day of April, 2007

JON W. DUDAS
*Director of the United States Patent and Trademark Office*